US009993495B2

(12) United States Patent
Guiducci et al.

(10) Patent No.: US 9,993,495 B2
(45) Date of Patent: Jun. 12, 2018

(54) INTRAPULMONARY ADMINISTRATION OF POLYNUCLEOTIDE TOLL-LIKE RECEPTOR 9 AGONISTS FOR TREATING CANCER OF THE LUNG

(71) Applicant: Dynavax Technologies Corporation, Berkeley, CA (US)

(72) Inventors: Cristiana Guiducci, Albany, CA (US); Robert L. Coffman, Portola Valley, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 131 days.

(21) Appl. No.: 15/162,535

(22) Filed: May 23, 2016

(65) Prior Publication Data
US 2016/0346312 A1    Dec. 1, 2016

Related U.S. Application Data

(60) Provisional application No. 62/276,767, filed on Jan. 8, 2016, provisional application No. 62/169,321, filed on Jun. 1, 2015, provisional application No. 62/169,309, filed on Jun. 1, 2015, provisional application No. 62/168,470, filed on May 29, 2015, provisional application No. 62/168,449, filed on May 29, 2015.

(51) Int. Cl.
| A61K 31/713 | (2006.01) |
| A61K 45/06 | (2006.01) |
| A61K 9/00 | (2006.01) |
| A61K 31/7125 | (2006.01) |

(52) U.S. Cl.
CPC .......... *A61K 31/713* (2013.01); *A61K 9/0073* (2013.01); *A61K 31/7125* (2013.01); *A61K 45/06* (2013.01)

(58) Field of Classification Search
CPC .. A61K 31/713; A61K 31/7125; A61K 45/06; A61K 9/0073
See application file for complete search history.

(56) References Cited

U.S. PATENT DOCUMENTS

| 7,745,606 B2 * | 6/2010 | Dina ...................... C07H 21/00 424/278.1 |
| 8,372,413 B2 | 2/2013 | Fearon et al. |
| 2010/0184834 A1 | 7/2010 | Dina et al. |
| 2017/0326232 A1 * | 11/2017 | Guiducci ............. A61K 39/395 |

FOREIGN PATENT DOCUMENTS

| CN | 101 134 046 A | 3/2008 |
| WO | WO-2004/058179 A2 | 7/2004 |
| WO | WO-2016/196062 A1 | 12/2016 |

OTHER PUBLICATIONS

Badie et al. (2013). "The future of CpG immunotherapy in cancer," Immunotherapy, 5(1):1-3.
Campbell et al. (2009). "CpG-containing immunostimulatory DNA sequences elicit TNF-α-dependent toxicity in rodents but not in humans." J Clin Invest, 119(9):2564-2576.
Campbell et al. (2014). "A limited CpG-containing oligodeoxynucleotide therapy regimen induces sustained suppression of allergic airway inflammation in mice" Thorax, 69(6):565-573.
Cheever et al. (2009). "The prioritization of cancer antigens: a national cancer institute pilot project for the acceleration of translational research." Clinical Cancer Research, 15(17):5323-5337.
Heppner et al. (2000). "Nontransgenic models of breast cancer." Breast Cancer Res, 2:331-334.
Kuzmov et al. (2015). "Nanotechnology approaches for inhalation treatment of lung diseases," J Control Release, 219:500-518.
Le Noci et al. (2015). "Poly(I:C) and CpG-ODN combined aerosolization to treat lung metastases and counter the immunosuppressive microenvironment," Oncolmmunology, 4:10, e1040214.
Lou et al. (2011). "Antitumor activity mediated by CpG: the route of administration is critical." J Immunother, 34(3):279-288.
Pramanick et al. (2013). "Excipient selection in parenteral formulation development," Pharma Times, 45(3):65-77.
Sandoval et al. (2013). "Mucosal imprinting of vaccine-induced CD8+ T cells is crucial to inhibit the growth of mucosal tumors." Sci Transl Med, 5(172):172ra20.
Sato et al. (2015). "Intrapulmonary delivery of CpG microparticles eliminates lung tumors." Mol Cancer Ther, 14(10):2198-2205.
Schmidt. (2007). "Clinical setbacks for toll-like receptor 9 agonists in cancer." Nature Biotechnology, 25(8):825-826.
Sfondrini et al. (2013). "Anti-tumor activity of CpG-ODN aerosol in mouse lung Metastases." Int J Cancer, 133:383-394.
International Preliminary Report on Patentability dated Dec. 14, 2017 for PCT Application No. PCT/US2016/033817 filed on May 23, 2016, eight pages.
International Search Report and Written Opinion dated Aug. 22, 2016 for PCT Application No. PCT/US2016/033817 filed on May 23, 2016, eleven pages.

* cited by examiner

Primary Examiner — Antonio Galisteo Gonzalez
(74) Attorney, Agent, or Firm — Morrison & Foerster LLP

(57) ABSTRACT

The present disclosure relates to methods for treating cancer by intrapulmonary administration of a polynucleotide Toll-like receptor 9 agonist. The methods of the present disclosure are suitable for treating primary cancer of the lung, as well as metastatic cancer to the lung and extra pulmonary cancers thereof. Additionally, the present disclosure provides polynucleotide Toll-like receptor 9 agonists with immune stimulatory and toxicity profiles suitable for intrapulmonary administration.

35 Claims, 8 Drawing Sheets

INTRAPULMONARY ADMINISTRATION OF POLYNUCLEOTIDE TOLL-LIKE RECEPTOR 9 AGONISTS FOR TREATING CANCER OF THE LUNG

CROSS-REFERENCE TO RELATED APPLICATIONS

This application claims benefit of U.S. Provisional Application No. 62/276,767, filed Jan. 8, 2016, which is incorporated by reference in its entirety. This application also claims benefit of U.S. Provisional Application Nos. 62/169,309 and 62/169,321, filed Jun. 1, 2015, and U.S. Provisional Application Nos. 62/168,449 and 62/168,470, filed May 29, 2015.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 377882006000SeqList.txt, date recorded: Jul. 25, 2016, size: 3 KB).

FIELD

The present disclosure relates to methods for treating cancer by intrapulmonary administration of a polynucleotide Toll-like receptor 9 agonist. The methods of the present disclosure are suitable for treating primary cancer of the lung, as well as metastatic cancer to the lung and extra pulmonary cancers thereof. Additionally, the present disclosure provides polynucleotide Toll-like receptor 9 agonists with immune stimulatory and toxicity profiles suitable for intrapulmonary administration.

BACKGROUND

According to the World Health Organization, cancer is a leading cause of death worldwide and lung cancer is one of the five most common cancers in both men and women. Despite advances made in treatment, unless diagnosed at an early clinical stage, the majority of lung cancer patients in the United States die within five years of diagnosis.

Polynucleotides containing unmethylated CG dinucleotides stimulate the innate immune system by activating cells expressing Toll-like receptor 9 (TLR9). Several polynucleotide TLR9 agonists have been tested as immunotherapeutic agents for cancer. While results of preclinical and phase II trials of a polynucleotide TLR9 agonist were promising, the polynucleotide TLR9 agonist did not improve survival of patients with non-small cell lung cancer when added to a chemotherapy regimen (Schmidt, Nature Biotechnology, 25:825-826, 2007). More recently, the route of administration of polynucleotide TLR9 agonists has been shown to be critical, with intratumoral injection resulting in superior antitumor immune responses than intravenous injection (Lou et al., J Immunother, 34:279-288, 2011).

Direct intratumoral injection of primary and metastatic tumors in the lung is generally not feasible. However, intrapulmonary delivery of polynucleotide TLR9 agonists has been shown to result in potent anti-tumor responses in mouse models of lung metastases (Sato et al., Mol Cancer Ther, 14:2198-2205, 2015; and Sfondrini et al., Inter J Cancer, 133:383-394, 2013). Even so, polynucleotide TLR9 agonists must have an appropriate therapeutic window for intrapulmonary administration to human cancer patients.

Thus, what the art needs are polynucleotide TLR9 agonists with high potency and low toxicity.

SUMMARY

The present disclosure relates to methods for treating cancer by intrapulmonary administration of a polynucleotide Toll-like receptor 9 agonist. The methods of the present disclosure are suitable for treating primary cancer of the lung, as well as metastatic cancer to the lung and extra pulmonary cancers thereof. Additionally, the present disclosure provides polynucleotide Toll-like receptor 9 agonists with immune stimulatory and toxicity profiles suitable for intrapulmonary administration.

Specifically, the present disclosure provides methods of treating cancer of the lung in a mammalian subject in need thereof, the method comprising administering to the subject an effective amount a polynucleotide by intrapulmonary delivery, wherein the polynucleotide consists of the sequence of: 5'-TCGTAACGTTCGAACGTTCGANx-3' (SEQ ID NO:2), wherein x is 0, 1 or 2, each N is A, C or T, and wherein at least one internucleotide linkage is a phosphorothioate linkage. In some preferred embodiments, the polynucleotide consists of SEQ ID NO:7, SEQ ID NO:8, or SEQ ID NO:9. In some embodiments, the polynucleotide is double-stranded, while in other embodiments, the polynucleotide is single-stranded. In some embodiments, all of the internucleotide linkages are phosphorothioate linkages. In some embodiments, the subject has a primary cancer selected from the group consisting of primary lung cancer and extrapulmonary cancer. In some embodiments, the cancer of the lung is primary lung cancer. In a subset of these embodiments, the primary lung cancer is non-small-cell lung carcinoma (NSCLC) or small-cell lung carcinoma (SCLC). In some embodiments, the cancer of the lung is metastatic cancer to the lung. In some embodiments, the metastatic cancer is a metastasis of a primary cancer selected from the group consisting of bladder cancer, breast cancer, colorectal cancer, head and neck cancer, kidney cancer, melanoma, pancreatic cancer, prostate cancer, and ovarian cancer. In preferred embodiments, the mammalian subject is a human. Additionally, the present disclosure provides methods which further comprise administering an effective amount of a second therapeutic agent to the subject. In some embodiments, the second therapeutic agent comprises a chemotherapeutic agent selected from the group consisting of actinomycin, afatinib, alectinib, asparaginase, azacitidine, azathioprine, bicalutamide, bleomycin, bortezomib, camptothecin, carboplatin, capecitabine, certinib, cisplatin, chlorambucil, crizotinib, cyclophosphamide, cytarabine, daunorubicin, docetaxel, doxifluridine, doxorubicin, erlotinib, epirubicin, epothilone, etoposide, fludarabine, flutamine, fluorouracil, gefitinib, gemcitabine, hydroxyurea, idarubicin, ifosfamide, imatinib, irinotecan, lapatinib, letrozole, mechlorethamine, mercaptopurine, methotrexate, mitomycin, mitoxantrone, octreotide, oxaliplatin, paclitaxel, pemetrexed, raltitrexed, sorafenib, sunitinib, tamoxifen, temozolomide, teniposide, tioguanine, topotecan, valrubicin, vinblastine, vincristine, vindesine, vinorelbine, and combinations thereof. In some embodiments, the chemotherapeutic agent comprises a combination selected from the group consisting of: i) cyclophosphamide, doxorubicin, and vincristine; ii) mitomycin, vindesine and cisplatin; iii) cisplatin and vinorelbine; and iv) cisplatin, etoposide and ifosfamide. In some embodiments, the second therapeutic agent comprises an antagonist of an inhibitory immune checkpoint molecule. In a subset of these embodiments, the inhibitory immune checkpoint molecule is selected from the group consisting of PD-1, PD-L1, PD-L2, CTLA-4 (CD152), LAG-3, TIM-3, TIGIT, IL-10, and TGF-beta. In some embodiments, the inhibitory immune checkpoint molecule is indoleamine 2,3-dioxygenase (IDO) or tryptophan 2,3-dioxygenase (TDO). In some embodiments, the second therapeutic agent comprises an agonist of an immune stimulatory molecule. In a subset of these embodiments, the immune stimulatory molecule is selected from the group consisting of CD27, CD40, OX40 (CD134), GITR, CD137, CD28 and ICOS (CD278). In some embodiments, the second therapeutic agent comprises a monoclonal antibody, fragment or derivative thereof. The present disclosure also provides methods which further comprise one or both of resecting the primary cancer and administering radiation therapy. In some particularly preferred embodiments, the effective amount of the polynucleotide and the effective amount of the second therapeutic agent together result in a synergistic effect against the cancer of the lung. In some preferred embodiments, the effective amount of the polynucleotide and the effective amount of the second therapeutic agent together result in an additive effect against the cancer of the lung. In some embodiments, the effective amount of the polynucleotide and the effective amount of the second therapeutic agent together result in a cooperative effect against the cancer of the lung. In some preferred embodiments, treating cancer of the lung comprises one or more of the following: (a) increasing survival time of the subject; (b) reducing volume of the primary cancer; (c) retarding growth of the primary cancer; (d) reducing number of metastatic tumors; (e) reducing volume of metastatic tumors; and (f) retarding growth of metastatic tumors. In some embodiments, treating cancer of the lung comprises inducing secretion in the lung of one or more cytokines selected from the group consisting of chemokine CC motif ligand 2 (CCL2), chemokine CXC motif ligand 10 (CXCL10), interferon-alpha (IFN-α), interferon-gamma (IFN-γ), interleukin-1alpha (IL-1α), interleukin-6 (IL-6), interleukin-10 (IL-10), interleukin-12 p70 (IL-12p70), granulocyte colony-stimulating factor (GCSF), and tumor necrosis factor-alpha (TNF-α). In some preferred embodiments, treating cancer of the lung does not result in polynucleotide-induced toxicity of the lung of such severity that repeated administration of the polynucleotide is contraindicated. In some preferred embodiments, treating cancer of the lung does not result in polynucleotide-induced flu-like symptoms of such severity that repeated administration of the polynucleotide is contraindicated, wherein the flu-like symptoms comprise one or more of the group consisting of fever, headache, chills, myalgia and fatigue.

Further more the present disclosure provides an isolated polynucleotide, wherein the polynucleotide consists of SEQ ID NO:7, SEQ ID NO:8, or SEQ ID NO:9, and wherein at least one internucleotide linkage is a phosphorothioate linkage. In some preferred embodiments, all of the internucleotide linkages are phosphorothioate linkages. Additionally, the present disclosure provides pharmaceutical compositions comprising the polynucleotide and a pharmaceutically acceptable excipient. In some embodiments, the composition is a sterile, isotonic solution. In other embodiments, the composition is a dehydrated solid. In some embodiments, the pharmaceutical composition further comprises a polypeptide antigen. In some preferred embodiments, the polypeptide antigen is a tumor antigen. The present disclosure also provides methods of stimulating an immune response in a mammalian subject, comprising: administering the pharmaceutical composition to the subject in an amount sufficient to stimulate the immune response in the subject. The present disclosure further provides methods of increasing interferon-alpha (IFN-α) in a mammalian subject, comprising: administering the pharmaceutical composition to the subject in an amount sufficient to increase IFN-α in the subject. Moreover, the present disclosure provides methods of treating cancer in a mammalian subject in need thereof, comprising: administering the pharmaceutical composition to the subject in an amount sufficient to treat cancer in the subject. In some preferred embodiments, the pharmaceutical composition is administered to the subject by intrapulmonary administration, which may involve use of a device selected from the group consisting of a nebulizer, a metered-dose inhaler, a sprayer, and a dry-powder inhalation device. In some preferred embodiments, the pharmaceutical composition is administered by injection through a route selected from the group consisting of intravenous, intramuscular, and subcutaneous.

DETAILED DESCRIPTION

Figure 1:
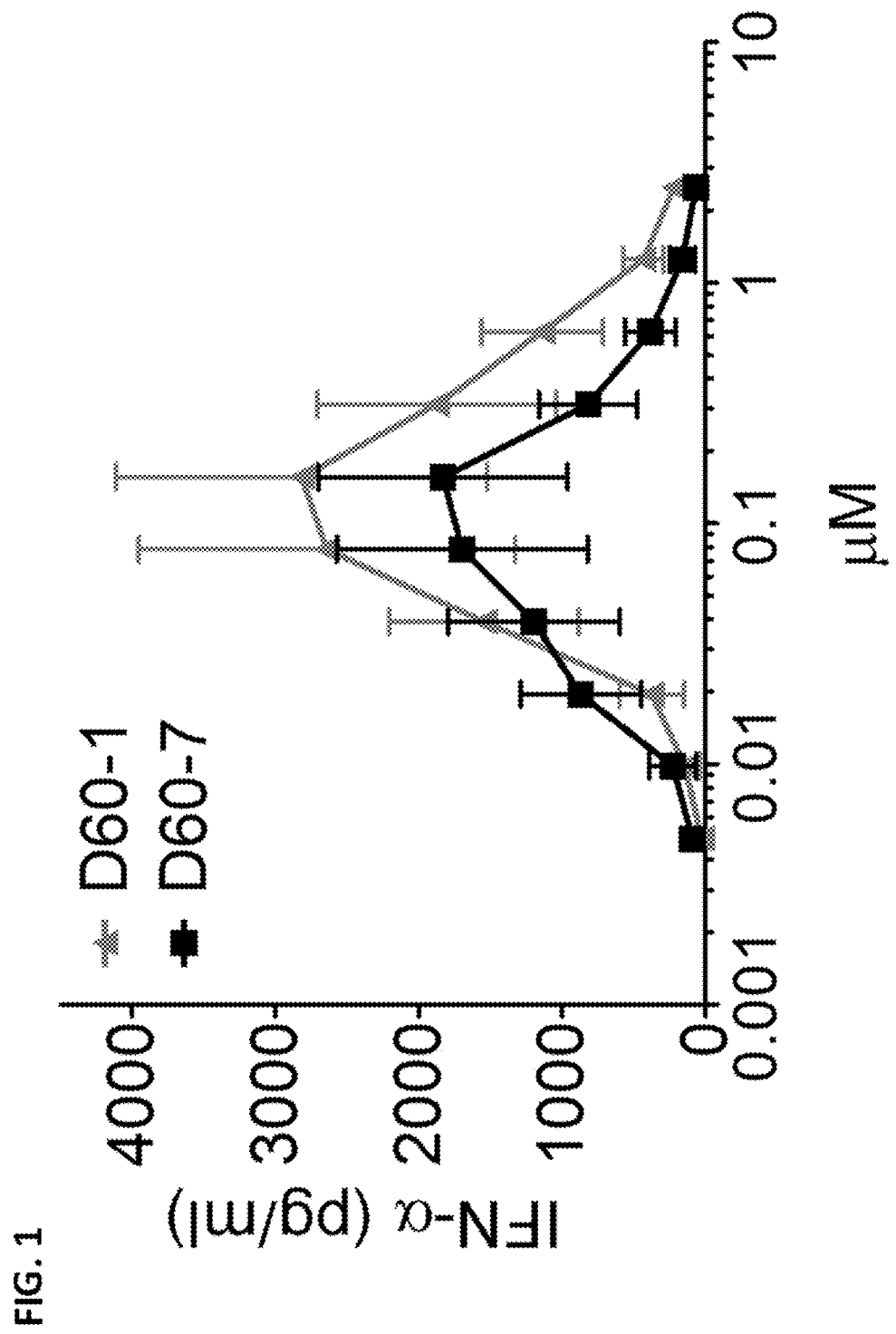
FIG. 1 is a graph depicting IFN-α production (pg/mL) by human PBMCs in response to increasing doses of polynucleotide TLR9 agonist D60-1 or TLR9 agonist D60-7. Data shown as Mean±SEM.

The present disclosure relates to methods for treating cancer by intrapulmonary administration of a polynucleotide Toll-like receptor 9 agonist. The methods of the present disclosure are suitable for treating primary cancer of the lung, as well as metastatic cancer to the lung and extra pulmonary cancers thereof. Additionally, the present disclosure provides polynucleotide Toll-like receptor 9 agonists with immune stimulatory and toxicity profiles suitable for intrapulmonary administration.

I. General Methods and Definitions

The practice of the present disclosure will employ, unless otherwise indicated, conventional techniques of molecular biology, microbiology, cell biology, biochemistry, nucleic acid chemistry, and immunology, which are within the skill of the art. Such techniques are fully described in the literature, see for example: *Animal Cell Culture*, sixth edition (Freshney, Wiley-Blackwell, 2010); *Antibodies, A Laboratory Manual*, second edition (Greenfield, ed., Cold Spring Harbor Publications, 2013); *Bioconjugate Techniques*, third edition (Hermanson, Academic Press, 1996); *Current Protocols in Cell Biology* (Bonifacino et al., ed., John Wiley & Sons, Inc., 1996, including supplements through 2014); *Current Protocols in Immunology* (Coligan et al., eds., John Wiley & Sons, Inc., 1991 including supplements through 2014); *Current Protocols in Molecular Biology* (Ausubel et al., eds., John Wiley & Sons, Inc., 1987, including supplements through 2014); *Current Protocols in Nucleic Acid Chemistry* (Egli et al., ed., John Wiley & Sons, Inc., 2000, including supplements through 2014); *Molecular Cloning: A Laboratory Manual*, third edition (Sambrook and Russell, Cold Spring Harbor Laboratory Press, 2001); *Molecular Cloning: A Laboratory Manual*, fourth edition (Green and Sambrook, Cold Spring Harbor Laboratory Press, 2012); *Oligonucleotide Synthesis: Methods and Applications* (Herdewijn, ed., Humana Press, 2004); *Protocols for Oligonucleotides and Analogs, Synthesis and Properties* (Agrawal, ed., Humana Press, 1993); and *Using Antibodies: A Laboratory Manual* (Harlow and Lane, Cold Spring Harbor Laboratory Press, 1998).

As used herein and in the appended claims, the singular forms "a," "an," and "the" include plural references unless indicated otherwise. For example, "an" excipient includes one or more excipients.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting of" and "consisting essentially of" embodiments.

The term "about" as used herein in reference to a value, encompasses from 90% to 110% of that value (e.g., about 20 µg survivin antigen refers to 18 µg to 22 µg survivin antigen and includes 20 µg survivin antigen).

As used interchangeably herein, the terms "polynucleotide," "oligonucleotide" and "nucleic acid" include single-stranded DNA (ssDNA), double-stranded DNA (dsDNA), single-stranded RNA (ssRNA) and double-stranded RNA (dsRNA), modified oligonucleotides and oligonucleosides, or combinations thereof. Polynucleotides are polymers of nucleosides joined, generally, through phosphodiester linkages, although alternate linkages, such as phosphorothioate esters may also be used. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, thymidine, and deoxycytidine. The four nucleoside units (or bases) in RNA are called adenosine, guanosine, uridine and cytidine. A nucleotide is a phosphate ester of a nucleoside.

The term "palindromic sequence" or "palindrome" refers to a nucleic acid sequence that is an inverted repeat, e.g., ABCDD'C'B'A', where the bases, e.g., A, and A', B and B', C and C', D and D', are capable of forming Watson-Crick base pairs. Such sequences may be single-stranded or may form double-stranded structures or may form hairpin loop structures under some conditions. For example, as used herein, "an 8 base palindrome" refers to a nucleic acid sequence in which the palindromic sequence is 8 bases in length, such as ABCDD'C'B'A'. A palindromic sequence may be part of a polynucleotide that also contains non-palindromic sequences. A polynucleotide may contain one or more palindromic sequence portions and one or more non-palindromic sequence portions. Alternatively, a polynucleotide sequence may be entirely palindromic. In a polynucleotide with more than one palindromic sequence portions, the palindromic sequence portions may or may not overlap with each other.

The terms "individual" and "subject" refer to mammals. "Mammals" include, but are not limited to, humans, non-human primates (e.g., monkeys), farm animals, sport animals, rodents (e.g., mice and rats) and pets (e.g., dogs and cats).

The term "antigen" refers to a substance that is recognized and bound specifically by an antibody or by a T cell antigen receptor. Antigens can include peptides, polypeptides, proteins, glycoproteins, polysaccharides, complex carbohydrates, sugars, gangliosides, lipids and phospholipids; portions thereof and combinations thereof. Antigens when present in the compositions of the present disclosure can be synthetic or isolated from nature. Antigens suitable for administration in the methods of the present disclosure include any molecule capable of eliciting an antigen-specific B cell or T cell response. Haptens are included within the scope of "antigen." A "hapten" is a low molecular weight compound that is not immunogenic by itself but is rendered immunogenic when conjugated with a generally larger immunogenic molecule (carrier).

"Polypeptide antigens" can include purified native peptides, synthetic peptides, recombinant peptides, crude peptide extracts, or peptides in a partially purified or unpurified active state (such as peptides that are part of attenuated or inactivated viruses, microorganisms or cells), or fragments of such peptides. Polypeptide antigens are preferably at least six amino acid residues in length.

As used herein, the term "immunogenic" refers to the ability of an agent (e.g., polypeptide antigen) to elicit an adaptive immune response upon administration under suitable conditions to a mammalian subject. The immune response may be B cell (humoral) and/or T cell (cellular) response.

"Adjuvant" refers to a substance which, when mixed with an immunogenic agent such as antigen, nonspecifically enhances or potentiates an immune response to the agent in the recipient upon exposure to the mixture.

The term "agonist" is used in the broadest sense and includes any molecule that activates signaling through a receptor. In some embodiments, the agonist binds to the receptor. For instance, a TLR9 agonist binds to a TLR9 receptor and activates a TLR9-signaling pathway. In another example, an agonist of the immune stimulatory molecule CD27 binds to and activates a CD27 signalling pathway.

The term "antagonist" is used in the broadest sense, and includes any molecule that blocks at least in part, a biological activity of an agonist. In some embodiments, the antagonist binds to the agonist, while in other embodiments, the antagonist binds to the ligand of the agonist. For example, an antagonist of the inhibitory immune checkpoint molecule PD-1 binds to and blocks a PD-1 signaling pathway.

The terms "immunostimulatory sequence" and "ISS" refer to a nucleic acid sequence that stimulates a measurable immune response (e.g., measured in vitro, in vivo, and/or ex vivo). For the purpose of the present disclosure, the term ISS refers to a nucleic acid sequence comprising an unmethylated CG dinucleotide. Examples of measurable immune responses include, but are not limited to, antigen-specific antibody production, cytokine secretion, lymphocyte activation and lymphocyte proliferation.

The terms "CpG" and "CG" are used interchangeably herein to refer to a cytosine and guanine separated by a phosphate. These terms refer to a linear sequence as opposed to base-pairing of cytosine and guanine. The polynucleotides of the present disclosure contain at least one unmethylated CpG dinucleotide. That is the cytosine in the CpG dinucleotide is not methylated (i.e., is not 5-methylcytosine).

The terms "antisense" and "antisense sequence" as used herein refer to a non-coding strand of a polynucleotide having a sequence complementary to the coding strand of mRNA. In preferred embodiments, the polynucleotides of the present disclosure are not antisense sequences, or RNAi molecules (miRNA and siRNA). That is in preferred embodiments, the polynucleotides of the present disclosure do not have significant homology (or complementarity) to transcripts (or genes) of the mammalian subjects in which they will be used. For instance, a polynucleotide of the present disclosure for modulating an immune response in a human subject is preferably less than 80% identical over its length to nucleic acid sequences of the human genome (e.g., a polynucleotide that is 50 nucleotides in length would share no more than 40 of the 50 bases with a human transcript). That is, in preferred embodiments, the polynucleotides are less than 80%, 75%, 70%, 65%, 60%, 55%, 50%, 45%, 40%, 35%, 30%, 25% or 20%, identical to nucleic acid sequences of mammalian subjects (e.g., such as humans, nonhuman primates, farm animals, dogs, cats, rabbits, rats, mice, etc.) in which they are to be used.

"Stimulation" of a response or parameter includes eliciting and/or enhancing that response or parameter when compared to otherwise same conditions except for a parameter of interest, or alternatively, as compared to another condition (e.g., increase in TLR-signaling in the presence of a TLR agonist as compared to the absence of the TLR agonist). For example, "stimulation" of an immune response means an increase in the response.

"Inhibition" of a response or parameter includes blocking and/or suppressing that response or parameter when compared to otherwise same conditions except for a parameter of interest, or alternatively, as compared to another condition (e.g., decrease in PD-1-signaling in the presence of a PD-1 ligand and a PD-1 antagonist as compared to the presence of the PD-1 ligand in the absence of the PD-1 antagonist). For example, "inhibition" of an immune response means a decrease in the response.

An "effective amount" of an agent disclosed herein is an amount sufficient to carry out a specifically stated purpose. An "effective amount" may be determined empirically in relation to the stated purpose. An "effective amount" or an "amount sufficient" of an agent is that amount adequate to affect a desired biological effect, such as a beneficial result, including a beneficial clinical result. The term "therapeutically effective amount" refers to an amount of an agent (e.g., polynucleotide TLR9 agonist) effective to "treat" a disease or disorder in a subject (e.g., a mammal such as a human).

An "effective amount" or an "amount sufficient" of an agent may be administered in one or more doses.

The terms "treating" or "treatment" of a disease refer to executing a protocol, which may include administering one or more drugs to an individual (human or otherwise), in an effort to alleviate a sign or symptom of the disease. Thus, "treating" or "treatment" does not require complete alleviation of signs or symptoms, does not require a cure, and specifically includes protocols that have only a palliative effect on the individual. As used herein, and as well-understood in the art, "treatment" is an approach for obtaining beneficial or desired results, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival of an individual not receiving treatment. "Palliating" a disease or disorder means that the extent and/or undesirable clinical manifestations of the disease or disorder are lessened and/or time course of progression of the disease or disorder is slowed, as compared to the expected untreated outcome. Further, palliation and treatment do not necessarily occur by administration of one dose, but often occur upon administration of a series of doses.

II. Polynucleotide Toll Like Receptor 9 (TLR9) Agonists

The present disclosure provides polynucleotides consisting of the sequence of: 5'-TCGTAACGTTCGAACGTTC-GANx-3' (SEQ ID NO:2), wherein x is 0, 1 or 2, each N is A, C or T, and wherein at least one internucleotide linkage is a phosphorothioate ester linkage. In some embodiments, the polynucleotide consists of the sequence of SEQ ID NO:7 (D60-7), SEQ ID NO:8 (D60-8), or SEQ ID NO:9 (D60-9). In some embodiments, one or more linkages between the nucleotides are phosphodiester linkages. In some embodiments, all of the linkages between the nucleotides are phosphorothioate ester linkages. In some embodiments, the polynucleotide is single-stranded. In other embodiments, the polynucleotide is double-stranded. In some embodiments, the polynucleotide is a 2'-deoxyribopolynucleotide.

The polynucleotides of SEQ ID NO:1 (D60-1) and SEQ ID NO:3 (D60-3) potently induce high levels of IFN-α from human PBMC. As such, these polynucleotides were deemed to be less desirable for intrapulmonary administration. The polynucleotides of the present disclosure were developed by gradually shortening the sequence and palindrome length of D60-3 by effectively removing nucleotides from the 3' end of D60-3 (see, Tables 1-1 and 1-2). Surprisingly, shorter variants of D60-3 were identified that induced lower maximum levels of IFN-α from human PBMC, while retaining potency (see Table 1-3). Reducing the palindrome by 8 bases and the sequence length by 4 bases in relation to D60-3 was not predicted to result in this desirable activity profile.

As demonstrated in the experimental examples, the polynucleotide TLR9 agonists of the present disclosure are particularly well suited for intrapulmonary administration in that they possess desirable stimulatory and toxicity profiles. Specifically, the polynucleotide TLR9 agonists of the present disclosure are potent inducers of moderate levels of IFN-α from mammalian PBMC, but are not associated with substantial toxicity even after repeated intrapulmonary delivery. As such, the polynucleotide TLR9 agonists of the present disclosure are expected to be efficacious at low doses, and are not expected to cause severe or life-threatening side effects that would necessitate dosage reduction, temporary treatment withdrawal, or permanent treatment discontinuation. The polynucleotide TLR9 agonists of the present disclosure are expected to be particularly useful for treating cancer of the lung, as detailed herein.

III. Pharmaceutical Compositions

Pharmaceutical compositions comprising a polynucleotide TLR9 agonist of the present disclosure are also provided. The pharmaceutical compositions routinely contain a pharmaceutically acceptable excipient. In some embodiments, the pharmaceutical compositions further comprise an antigen. Pharmaceutical compositions of the present disclosure may be in the form of a solution. Alternatively, the pharmaceutical compositions may be a dehydrated solid (e.g., freeze dried or spray dried solid). The pharmaceutical compositions of the present disclosure are preferably sterile, and preferably essentially endotoxin-free. The term "pharmaceutical composition" is used interchangeably herein with the terms "medicinal product" and "medicament."

A. Excipients

Pharmaceutically acceptable excipients of the present disclosure include for instance, solvents, bulking agents, buffering agents, tonicity adjusting agents, and preservatives (see, e.g., Pramanick et al., Pharma Times, 45:65-77, 2013). In some embodiments the pharmaceutical compositions may comprise an excipient that functions as one or more of a solvent, a bulking agent, a buffering agent, and a tonicity adjusting agent (e.g., sodium chloride in saline may serve as both an aqueous vehicle and a tonicity adjusting agent). The pharmaceutical compositions of the present disclosure are suitable for parenteral administration. That is the pharmaceutical compositions of the present disclosure are not intended for enteral administration.

In some embodiments, the pharmaceutical compositions comprise an aqueous vehicle as a solvent. Suitable vehicles include for instance sterile water, saline solution, phosphate buffered saline, and Ringer's solution. In some embodiments, the composition is isotonic.

The pharmaceutical compositions may comprise a bulking agent. Bulking agents are particularly useful when the pharmaceutical composition is to be lyophilized before administration. In some embodiments, the bulking agent is a protectant that aids in the stabilization and prevention of degradation of the active agents during freeze or spray drying and/or during storage. Suitable bulking agents are sugars (mono-, di- and polysaccharides) such as sucrose, lactose, trehalose, mannitol, sorbital, glucose and raffinose.

The pharmaceutical compositions may comprise a buffering agent. Buffering agents control pH to inhibit degradation of the active agent during processing, storage and optionally reconstitution. Suitable buffers include for instance salts comprising acetate, citrate, phosphate or sulfate. Other suitable buffers include for instance amino acids such as arginine, glycine, histidine, and lysine. The buffering agent may further comprise hydrochloric acid or sodium hydroxide. In some embodiments, the buffering agent maintains the pH of the composition within a range of 4 to 9. In some embodiments, the pH is greater than (lower limit) 4, 5, 6, 7 or 8. In some embodiments, the pH is less than (upper limit) 9, 8, 7, 6 or 5. That is, the pH is in the range of from about 4 to 9 in which the lower limit is less than the upper limit.

The pharmaceutical compositions may comprise a tonicity adjusting agent. Suitable tonicity adjusting agents include for instance dextrose, glycerol, sodium chloride, glycerin and mannitol.

The pharmaceutical compositions may comprise a preservative. Suitable preservatives include for instance antioxidants and antimicrobial agents. However, in preferred embodiments, the pharmaceutical composition is prepared under sterile conditions and is in a single use container, and thus does not necessitate inclusion of a preservative.

B. Antigens

The present disclosure further provides pharmaceutical compositions comprising an antigen and an excipient in addition to a polynucleotide TLR9 agonist. In preferred compositions of the present disclosure comprising an antigen, the antigen is not covalently-linked to the polynucleotide. In some preferred embodiments, the antigen is a polypeptide antigen. In some preferred embodiments, the antigen is a polysaccharide antigen, which is preferably covalently attached to a carrier protein. In some preferred embodiments, the antigen is a tumor antigen. In other embodiments, the antigen is a microbial antigen or an allergen.

The pharmaceutical compositions may comprise a tumor antigen. In some embodiments, the tumor antigen is a mammalian antigen. Suitable tumor antigens have been described in the art (see, e.g., Cheever et al., Clinical Cancer Research, 15:5323-5337, 2009). For instance, suitable tumor antigens include WT1, MUC1, LMP2, HPV E6 E7, EGFRvIII, Her-2/neu, idiotype, MAGE A3, p53, NY-ESO-1, PSMA, GD2, CEA, MelanA/Marti, Ras, gp100, proteinase3 (PR1), bcr-able, tyrosinase, survivin, PSA, hTERT, sarcoma translocation breakpoints, EphA2, PAP, MP-IAP, AFP, EpCAM, ERG, NA17, PAX3, ALK, androgen receptor, cyclin B1, polysialic acid, MYCN, PhoC, TRP-2, GD3, Fucosyl, GM1, mesothelin, PSCA, MAGE A1, sLe(a), CYP1B1, PLAC1, GM3, BORIS, Tn, GloboH, ETV6-AML, NY-BR-1, RGS5, SART3, STn, cabonic anhydrase IX, PAX5, OY-TES 1, sperm protein 17, LCK, HMWMAA, AKAP-4, SSX2, XAGE 1, B7H3, legumain, Tie 2, Page4, VEGFR2, MAD-CT-1, FAP, PDGFR-beta, MAD-CT-2, and Fos-related antigen 1.

The pharmaceutical compositions may comprise a microbial antigen selected from the group consisting of a viral antigen, a bacterial antigen, a fungal antigen and a parasite antigen. In some preferred embodiments, the microbial antigen is a viral antigen or a bacterial antigen. In some embodiments, the microbial antigen is from a microbe that causes an infectious disease in a nonhuman, mammalian subject. In some embodiments, the microbial antigen is from a microbe that causes an infectious disease in a human subject. In some embodiments, the infectious disease is caused by a virus, a bacterium, a fungus or a protozoan parasite.

The pharmaceutical compositions may comprise an allergen. In some embodiments, the allergen is an environmental antigen such as mammalian, insect, plant and mold allergens. In some embodiments, the mammalian allergen includes fur and dander.

C. Kits

Additionally, the present disclosure provides kits that comprise a pharmaceutical composition (comprising an excipient and a polynucleotide TLR9 agonist) and a set of instructions relating to the use of the composition for the methods describe herein. The pharmaceutical composition of the kits is packaged appropriately. For example, if the pharmaceutical composition is a freeze-dried power, a vial with a resilient stopper is normally used so that the powder may be easily resuspended by injecting fluid through the resilient stopper. In some embodiments, the kits further comprise a device for administration (e.g., syringe and needle, nebulizer, dry powder inhalation device, etc.) of the pharmaceutical composition. The instructions relating to the use of the pharmaceutical composition generally include information as to dosage, schedule and route of administration for the intended methods of use. In some embodiments, in which the kits comprise an antigen, the antigen may or may not be packaged in the same container as the polynucleotide TLR9 agonist.

IV. Methods of Use

The pharmaceutical compositions of the present disclosure are suitable for a plurality of uses involving stimulating an immune response in a mammalian subject in need thereof. Mammalian subjects include but are not limited to humans, nonhuman primates, rodents, pets, and farm animals. In some embodiments, the pharmaceutical compositions may be administered to the subject in an amount effective to achieve a specific outcome.

A. Dosage and Mode of Administration

As with all pharmaceutical compositions, the effective amount and mode of administration may vary based on several factors evident to one skilled in the art. An important factor to be considered is whether the pharmaceutical composition is to be administered as a stand-alone treatment, or as part of a combination of therapeutic agents. Another factor is whether the pharmaceutical composition further contains an antigen. Other factors to be considered include the outcome to be achieved, and the number of doses to be administered.

A suitable dosage range is one that provides the desired effect. Dosage may be determined by the amount of polynucleotide administered to the subject. An exemplary dosage range of the polynucleotide given in amount to be delivered by subject weight is from about 5 to 5000 mcg/kg. In some embodiments, the dosage is greater than about (lower limit) 5, 10, 50, 100, 150, 200, 250, 300, 350, 400, 450, 500, 750 or 1000 mcg/kg. In some embodiments, the dosage is less than about (upper limit) 5000, 4000, 3000, 2000, 1000, 750, 500, 450, 400, 350, 300, 250, 200, 150, or 100 mcg/kg. That is, the dosage is anywhere in the range of from about 5 to 5000 mcg/kg in which the lower limit is less than the upper limit. An exemplary dosage range of the polynucleotide given in amount to be delivered to a human subject is from about 100 mcg to about 100 mg. In some embodiments, the dosage is greater than about (lower limit) 100, 250, 500, 750, 1000, 1500, 2000, 2500, 3000, 3500, 4000, 4500, or 5000 mcg. In some embodiments, the dosage is less than about (upper limit) 100, 75, 50, 25, 20, 15, or 10 mg. That is, the dosage is anywhere in the range of from about 100 to 100,000 mcg in which the lower limit is less than the upper limit.

In some embodiments, when the pharmaceutical composition further comprises an antigen, the antigen dosage range given in amount to be delivered to a subject is from about 1 mcg to 50 mcg. In some embodiments, the antigen dosage is greater than about (lower limit) 1, 5, 10, 15, 20, 25, 30, 35 or 40 mcg. In some embodiments, the antigen dosage is less than about (upper limit) 50, 45, 40, 35, 30, 25, 20, 15, or 10 mcg. That is, the antigen dosage is anywhere in the range of from about 1 to 50 mcg in which the lower limit is less than the upper limit.

In some embodiments, the pharmaceutical compositions of the present disclosure are intended for parenteral administration (e.g., not oral or rectal administration). Suitable routes of administration include injection, topical, and inhalation. In particular, the pharmaceutical compositions of the present disclosure may be administered by a route such as intravenous, intramuscular, subcutaneous, epidermal (gene gun), transdermal, and inhalation.

In some preferred embodiments, the pharmaceutical compositions of the present disclosure are intended for intrapulmonary administration (also referred to herein as pulmonary administration). Intrapulmonary administration is preferred for treatment of diseases of the lung, such as cancer of the lung, to achieve local delivery of the therapeutic polynucleotide to the intended site of action while reducing the likelihood of adverse systemic side effects. Devices suitable for intrapulmonary administration include nebulizers, metered-dose inhalers, sprayers, and dry-powder inhalation devices.

A suitable dosing regimen is one that provides the desired effect in a prophylactic or therapeutic context. The number of doses administered by a chosen route may be one or more than one. Frequency of dosing may range from weekly, bi-weekly, monthly, bi-monthly, or 3 to 12 months between doses. In some embodiments, 2 doses are administered with the second dose being administered one to two months after the first dose. In some embodiments, 3 doses are administered with the second dose being administered one to two months after the first dose, and the third dose being administered one to five months after the second dose. In other embodiments, 3, or 4 doses may be administered on a bi-weekly or monthly basis. In other embodiments, a shorter or longer period of time may elapse in between doses. In certain embodiments, the interval between successive dosages may vary in terms of number of weeks or number of months. In one embodiment, a series of 2, 3, 4, 5, or 6 weekly doses may be administered followed by a second series of a number of weekly doses at a later time point. One of skill in the art will be able to adjust the dosage regimen by measuring biological outcomes as exemplified in the examples, such as antigen-specific antibody responses or tumor regression.

B. Stimulation of an Immune Response

In brief, the present disclosure provides methods of stimulating an immune response in a mammalian subject, comprising administering to a mammalian subject a pharmaceutical composition in an amount sufficient to stimulate an immune response in the mammalian subject. "Stimulating" an immune response, means increasing the immune response, which can arise from eliciting a de novo immune response (e.g., as a consequence of an initial vaccination regimen) or enhancing an existing immune response (e.g., as a consequence of a booster vaccination regimen). In some embodiments, stimulating an immune response comprises one or more of the group consisting of: stimulating cytokine production; stimulating B lymphocyte proliferation; stimulating interferon pathway-associated gene expression; stimulating chemoattractant-associated gene expression; and stimulating plasmacytoid dendritic cell (pDC) maturation. Methods for measuring stimulation of an immune response are known in the art and described in the biological examples of the present disclosure. In embodiments in which the pharmaceutical composition further comprises an antigen, stimulating an immune response comprises inducing an antigen-specific antibody response.

For instance, in some embodiments in which the pharmaceutical composition further comprises an antigen, the present disclosure provides methods of inducing an antigen-specific antibody response in a mammalian subject by administering to a mammalian subject the pharmaceutical composition in an amount sufficient to induce an antigen-specific antibody response in the mammalian subject. "Inducing" an antigen-specific antibody response means increasing titer of the antigen-specific antibodies above a threshold level such as a pre-administration baseline titer or a seroprotective level.

Analysis (both qualitative and quantitative) of the immune response can be by any method known in the art, including, but not limited to, measuring antigen-specific antibody production (including measuring specific antibody subclasses), activation of specific populations of lymphocytes such as B cells and helper T cells, production of cytokines such as IFN-alpha, IL-6, IL-12 and/or release of histamine. Methods for measuring antigen-specific antibody responses include enzyme-linked immunosorbent assay (ELISA). Activation of specific populations of lymphocytes can be measured by proliferation assays, and with fluorescence-activated cell sorting (FACS). Production of cytokines can also be measured by ELISA.

Preferably, a Th1-type immune response is stimulated (i.e., elicited or enhanced). With reference to present disclosure, stimulating a Th1-type immune response can be determined in vitro or ex vivo by measuring cytokine production from cells treated with an active agent of the present disclosure (polynucleotide TLR9 agonist) as compared to control cells not treated with the active agent. Examples of "Th1-type cytokines" include, but are not limited to, IL-2, IL-12, IFN-gamma and IFN-alpha. In contrast, "Th2-type cytokines" include, but are not limited to, IL-4, IL-5, and IL-13. Cells useful for the determination of immunostimulatory activity include cells of the immune system, such as antigen presenting cells lymphocytes, preferably macrophages and T cells. Suitable immune cells include primary cells such as peripheral blood mononuclear cells, including plasmacytoid dendritic cells and B cells, or splenocytes isolated from a mammalian subject.

Stimulating a Th1-type immune response can also be determined in a mammalian subject treated with an active agent of the present disclosure (polynucleotide TLR9 agonist) by measuring levels of IL-2, IL-12, and interferon before and after administration or as compared to a control subject not treated with the active agent. Stimulating a Th1-type immune response can also be determined by measuring the ratio of Th1-type to Th2-type antibody titers. "Th1-type" antibodies include human IgG1 and IgG3, and murine IgG2a. In contrast, "Th2-type" antibodies include human IgG2, IgG4 and IgE and murine IgG1 and IgE.

Cancer

The present disclosure provides methods of treating cancer in a mammalian subject, comprising administering to a mammalian subject a pharmaceutical composition comprising a polynucleotide TLR9 agonist in an amount sufficient to treat cancer in the mammalian subject. "Treating" cancer means to bring about a beneficial clinical result such as causing remission or otherwise prolonging survival as compared to expected survival in the absence of treatment. In some embodiments, when the cancer is a solid tumor, "treating" cancer comprises shrinking the size of the solid tumor or otherwise reducing viable cancer cell numbers. In other embodiments, when the cancer is a solid tumor, "treating" cancer comprises delaying growth of the solid tumor. In some preferred embodiments, the present disclosure provides methods of treating cancer of the lung in a mammalian subject in need thereof, comprising administering to the subject an effective amount of a polynucleotide TLR9 agonist of the present disclosure by intrapulmonary delivery. In some embodiments, the polynucleotide is present in a pharmaceutical composition further comprising an excipient.

The cancer of the lung may be primary lung cancer or metastatic cancer to the lung. In some embodiments, the subject has a primary cancer selected from the group consisting of primary lung cancer and extrapulmonary cancer. In some embodiments, the primary lung cancer is small-cell lung carcinoma (SCLC), while in other embodiments the primary lung cancer is non-small-cell lung carcinoma (NSCLC). The three main types of NSCLC are adenocarcinoma, squamous-cell carcinoma and large-cell carcinoma. Metastatic cancer to the lung is a secondary cancer that has spread to the lung from a primary cancer at a distant site. In some embodiments, the metastatic cancer is a metastasis of a primary cancer selected from the group consisting of bladder cancer, breast cancer, colorectal cancer, head and neck cancer, kidney cancer, melanoma, pancreatic cancer, prostate cancer, and ovarian cancer. In other embodiments, the metastatic cancer is from a cancer of unknown primary origin.

In some embodiments, the polynucleotide is administered as a sole therapeutic agent (monotherapy), while in other embodiments, the polynucleotide is administered in conjunction with an effective amount of a second therapeutic agent (combination therapy). Each therapeutic agent in a combination therapy may be administered simultaneously (in the same pharmaceutical composition), concurrently (in separate pharmaceutical compositions administered one after the other in any order) or sequentially in any order (in separate pharmaceutical compositions administered on separate occasions). Sequential administration is particularly useful when the therapeutic agents in the combination therapy are in different dosage forms (e.g., one agent is a dry powder for pulmonary administration and the other agent is a solution for administration by injection). Sequential administration is also useful when the therapeutic agents in the combination therapy are administered on different dosing schedules (e.g., one agent is a polynucleotide that is administered once every one, two, three or four weeks, and the other agent is a chemotherapeutic agent that is administered daily or more frequently. In some embodiments, the polynucleotide is administered in conjunction with surgical resection of the primary cancer, and may be administered before, during and/or after surgery. In some embodiments, surgical resection is a lobectomy, while in others the surgical resection is a wedge resection (sublobar excision).

The present disclosure provides combination therapies comprising the polynucleotide as a first therapeutic agent and a second therapeutic agent. In some embodiments, the second therapeutic agent comprises one of the group consisting of a chemotherapeutic agent, a biologic agent, and combinations thereof. In some embodiments, the methods further comprise one or both of resecting the primary cancer and administering radiation therapy. The second therapeutic agent is administered at a dose and schedule as approved by a relevant governmental agency (e.g., FDA, EMA, etc.) for use as a monotherapy. Alternatively, the second therapeutic agent is administered at a lower dose and/or less frequent schedule than approved by a relevant governmental agency for use as a monotherapy.

In some embodiments, the chemotherapeutic agent is selected from the group consisting of actinomycin, afatinib, alectinib, asparaginase, azacitidine, azathioprine, bicalutamide, bleomycin, bortezomib, camptothecin, carboplatin, capecitabine, certinib, cisplatin, chlorambucil, crizotinib, cyclophosphamide, cytarabine, daunorubicin, docetaxel, doxifluridine, doxorubicin, erlotinib, epirubicin, epothilone, etoposide, fludarabine, flutamine, fluorouracil, gefitinib, gemcitabine, hydroxyurea, idarubicin, ifosfamide, imatinib, irinotecan, lapatinib, letrozole, mechlorethamine, mercaptopurine, methotrexate, mitomycin, mitoxantrone, octreotide, oxaliplatin, paclitaxel, pemetrexed, raltitrexed, sorafenib, sunitinib, tamoxifen, temozolomide, teniposide, tioguanine, topotecan, valrubicin, vinblastine, vincristine, vindesine, vinorelbine, and combinations thereof.

In some embodiments, the biologic agent is a cytokine or an antibody. The cytokine or antibody may be a fragment, a derivative or a fusion protein. In some embodiments, the antibody is a monoclonal antibody, preferably a fully human monoclonal antibody or a humanized monoclonal antibody. In some embodiments, the antibody is an anti-EGF antibody, such as necitumumab.

The present disclosure provides combination therapies comprising a polynucleotide as a first therapeutic agent, and a second therapeutic agent comprising an antagonist of an inhibitory immune checkpoint molecule. In some embodiments, the inhibitory immune checkpoint molecule is selected from the group consisting of PD-1, PD-L1, PD-L2, CTLA-4 (CD152), LAG-3, TIM-3, TIGIT, IL-10, and TGF-beta. In other embodiments, the inhibitory immune checkpoint molecule is indoleamine 2,3-dioxygenase (IDO) or tryptophan 2,3-dioxygenase (TDO).

In still further embodiments, the present disclosure provides combination therapies comprising a polynucleotide as a first therapeutic agent, and a second therapeutic agent comprising an agonist of an immune stimulatory molecule. In some embodiments, the immune stimulatory molecule is selected from the group consisting of CD27, CD40, OX40 (CD134), GITR, CD137, CD28 and ICOS (CD278).

Preferably, the effective amount of the polynucleotide and the effective amount of the second therapeutic agent together result in a cooperative effect against the cancer of the lung. A cooperative effect is an effect that is greater than the effect resulting from administration of the polynucleotide in the absence of the second therapeutic agent, but is less than an additive effect. More preferably, the effective amount of the polynucleotide and the effective amount of the second therapeutic agent together result in an additive effect against the cancer of the lung. An additive effect is an effect that is approximately the sum of the effects resulting from administration of the polynucleotide and the second therapeutic agent as monotherapies, but is less than a synergistic effect. Even more preferably, the effective amount of the polynucleotide and the effective amount of the second therapeutic agent together result in a synergistic effect against the cancer of the lung. A synergistic effect is an effect that is greater than the sum of the effects resulting from administration of the polynucleotide and the second therapeutic agent as monotherapies.

The present disclosure provides methods for treating cancer of the lung either as a monotherapy or a combination therapy comprising a polynucleotide TLR9 agonist. Some methods achieve complete or partial remission for a period of time after cessation of therapy. In some embodiments, the method achieves one or more of the following outcomes:
(a) increasing survival time of the subject;
(b) reducing volume of the primary cancer;
(c) retarding growth of the primary cancer;
(d) reducing number of metastatic tumors;
(e) reducing volume of metastatic tumors; and
(f) retarding growth of metastatic tumors;
wherein the primary cancer is pulmonary or extrapulmonary.
In some embodiments, treating cancer of the lung comprises inducing secretion in the lung of one or more cytokines selected from the group consisting of one or more cytokines selected from the group consisting of chemokine CC motif ligand 2 (CCL2), chemokine CXC motif ligand 10 (CXCL10), interferon-alpha (IFN-α), interferon-gamma (IFN-γ), interleukin-1alpha (IL-1α), interleukin-6 (IL-6), interleukin-10 (IL-10), interleukin-12 p70 (IL-12p70), granulocyte colony-stimulating factor (GCSF), and tumor necrosis factor-alpha (TNF-α). In some embodiments, treating cancer of the lung does not result in polynucleotide-induced toxicity of the lung of such severity that repeated administration of the polynucleotide is contraindicated. In some embodiments, treating cancer of the lung does not result in polynucleotide-induced flu-like symptoms of such severity that repeated administration of the polynucleotide is contraindicated, wherein the flu-like symptoms comprise one or more of the group consisting of fever, headache, chills, myalgia and fatigue.

Other Diseases and Disorders

The present disclosure further provides methods of preventing an infectious disease in a mammalian subject, comprising administering to a mammalian subject a pharmaceutical composition of the present disclosure in an amount sufficient to prevent an infectious disease in the mammalian subject. That is, in some embodiments, the present disclosure provides prophylactic vaccines. In some embodiments, the mammalian subject is at risk of exposure to an infectious agent. "Preventing" an infectious disease means to protect a subject from developing an infectious disease. In some embodiments, preventing an infectious disease further comprises protecting a subject from being infected with an infectious agent (e.g., protecting a subject from developing an acute or a chronic infection). Additionally the present disclosure provides methods of ameliorating a symptom of an infectious disease in a mammalian subject, comprising administering to a mammalian subject a pharmaceutical composition in an amount sufficient to ameliorate a symptom of an infectious disease in the mammalian subject. That is, in some embodiments the present disclosure provides therapeutic vaccines. In some embodiments, the subject is acutely or chronically infected with an infectious agent. The infectious disease may be a viral, bacterial, fungal or parasitic disease. In some embodiments, the pharmaceutical composition may further comprise a viral, bacterial, fungal or parasitic antigen. "Ameliorating" a symptom of an infectious disease means to improve a symptom, preferably diminishing extent of the disease.

Moreover the present disclosure provides methods of ameliorating a symptom of an IgE-related disorder in a mammalian subject, comprising administering to the mammalian subject a pharmaceutical composition of the present disclosure in an amount sufficient to ameliorate a symptom of an IgE-related disorder in the mammalian subject. In some preferred embodiments, the IgE-related disorder is an allergy. Allergies include but are not limited to allergic rhinitis (hay fever), sinusitis, eczema, and hives. In some embodiments, the pharmaceutical composition may further comprise an allergen. "Ameliorating" a symptom of an IgE-related disorder means to improve a symptom, preferably diminishing extent of the disorder. For instance, if the IgE-related disorder is allergic rhinitis, ameliorating a symptom means to reduce swelling of nasal mucosa, reduce rhinorrhea (runny nose), and/or reduce sneezing.

EXAMPLES

Abbreviations: CTRL (control); DNA (deoxyribonucleic acid); BALF (bronchoalveolar lavage fluid); ELISA (enzyme-linked immunosorbent assay); $EC_{50}$ (half maximal effective concentration); (FACS) fluorescence-activated cell sorting; mcg or μg (microgram); PBMC (peripheral blood mononuclear cell); PN (polynucleotide); TLR9 (Toll-like receptor 9); and WT (wild type).

Although the foregoing disclosure has been described in some detail by way of illustration and example for purposes of clarity and understanding, it will be apparent to those skilled in the art that certain changes and modifications may be practiced. Therefore, descriptions and examples should not be construed as limiting the scope of the disclosure.

TABLE 1-1

Polynucleotide Sequences^

| PN | SEQ ID NO: | Sequence |
|---|---|---|
| D60-1 | 1 | 5'-TCG AAC GTT CGA ACG TTC GAA CGT TCG AAT-3' |
| D60-2 | 2 | 5'-TCG TAA CGT TCG AAC GTT CGA Nx-3' |
| D60-3 | 3 | 5'-TCG TAA CGT TCG AAC GTT CGA ACG TTA-3' |
| D60-4 | 4 | 5'-TCG TAA CGT TCG AAC GTT CGA ACG TT-3' |
| D60-5 | 5 | 5'-TCG TAA CGT TCG AAC GTT CGA ACG T-3' |
| D60-6 | 6 | 5'-TCG TAA CGT TCG AAC GTT CGA ACG-3' |
| D60-7 | 7 | 5'-TCG TAA CGT TCG AAC GTT CGA AC-3' |
| D60-8 | 8 | 5'-TCG TAA CGT TCG AAC GTT CGA A-3' |
| D60-9 | 9 | 5'-TCG TAA CGT TCG AAC GTT CGA-3' |

^The longest possible palindrome is shown in bold. At least one internucleotide linkage is a phosphorothioate linkage in D60-2 and in SEQ ID NO: 2, x is 0, 1, or 2, and N is A, C, or T.

TABLE 1-2

Polynucleotide Properties

| PN | SEQ ID NO: | # CpGs | Polynucleotide Length | Palindrome Length |
|---|---|---|---|---|
| D60-1 | 1 | 7 | 30 | 28 |
| D60-2 | 2 | 5 | 21-24 | 12-16 |
| D60-3 | 3 | 6 | 27 | 24 |
| D60-4 | 4 | 6 | 26 | 22 |
| D60-5 | 5 | 6 | 25 | 20 |
| D60-6 | 6 | 6 | 24 | 18 |
| D60-7 | 7 | 5 | 23 | 16 |
| D60-8 | 8 | 5 | 22 | 14 |
| D60-9 | 9 | 5 | 21 | 12 |

Table 1-1 shows the nucleotide sequences and Table 1-2 summarizes the sequence characteristics of the polynucleotide TLR9 agonists referred to in the examples. Unless otherwise noted, the polynucleotides are 2'-deoxyribopolynucleotides and the internucleotide linkages are phosphorothioate ester linkages.

Example 1

Isolation and Stimulation of Human Leukocytes by Polynucleotides

Activity of polynucleotides (PN) was assessed in vitro by measurement of cytokine secretion by human peripheral blood mononuclear cells (PBMCs) and isolated B cells.

PBMCs were isolated from blood of healthy human donors using Ficoll-Paque. B cells were isolated from buffy coats by positive selection using anti-CD19 microbeads (Miltenyi Biotec, Auburn, Calif.) according to the manufacturer's instructions. For IFN-α induction, duplicate cultures of PBMCs ($2.5 \times 10^6$ cells/mL) were incubated for 24 hours with increasing concentrations of polynucleotides. IFN-α levels in cell culture supernatants were measured by ELISA (n=4 donors). For IL-6 induction, duplicate cultures of B cells ($0.75 \times 10^6$ cells/mL) were incubated for 96 hours with increasing concentrations of polynucleotides. IL-6 levels in cell culture supernatants were measured by ELISA (n=12 donors).

Figure 2:
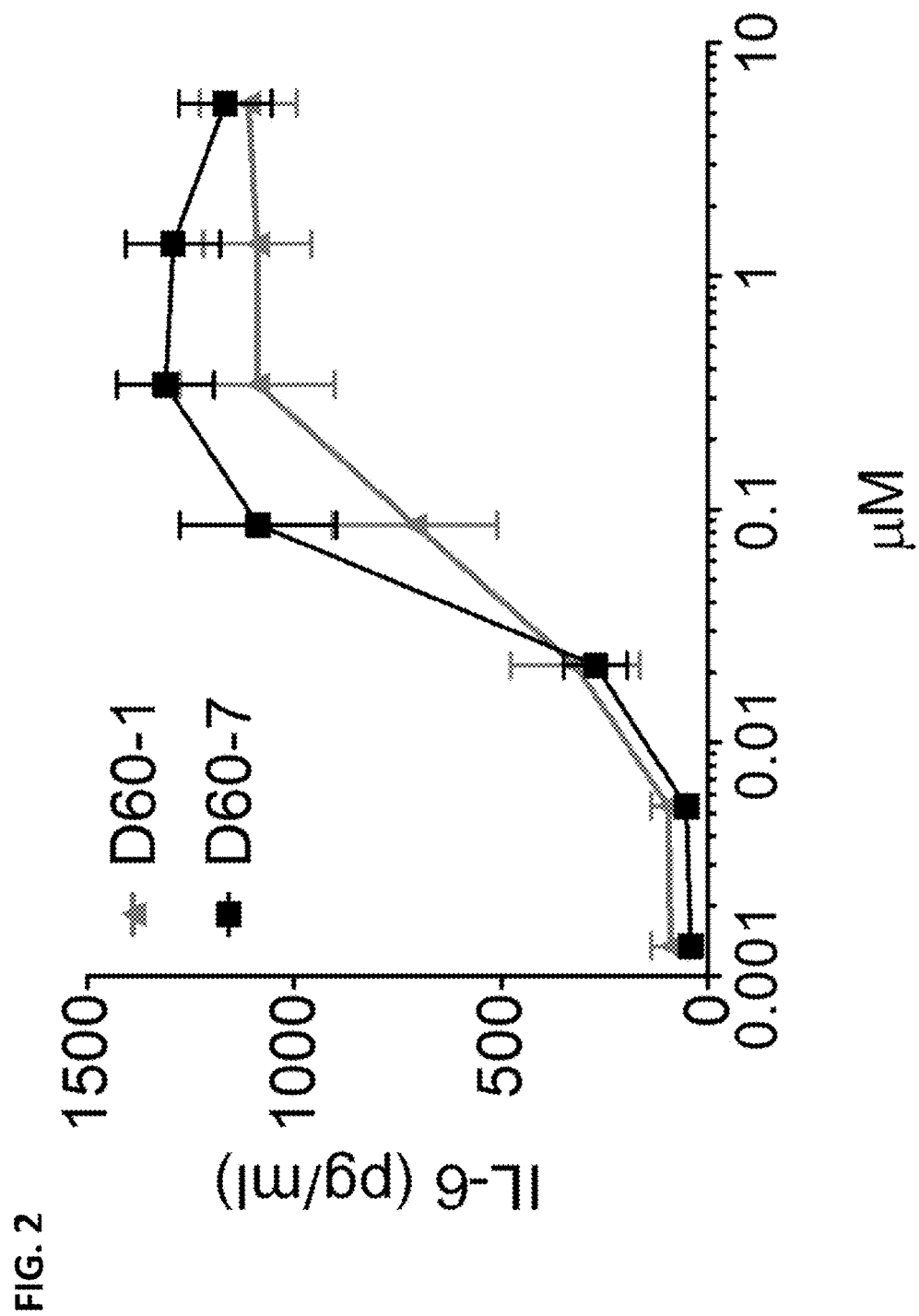
FIG. 2 is a graph depicting IL-6 production (pg/mL) by human B lymphocytes in response to increasing doses of polynucleotide TLR9 agonist D60-1 or TLR9 agonist D60-7. Data shown as Mean±SEM.

All polynucleotides tested induced IFN-α production from human PBMCs over a broad concentration range (FIG. 1). While D60-1 induced a higher maximum IFN-α level compared to D60-7, D60-7 was no less potent in that D60-1 and D60-7 had comparable IFN-α $EC_{50}$ values as shown in Table 1-3. Both D60-1 and D60-7 also induced IL-6 production from human B cells over a broad concentration range (FIG. 2). D60-7 induced a slightly higher maximal IL-6 level compared to D60-1.

TABLE 1-3

IFN-α Secretion by Human PBMC

| Polynucleotide | IFN-α $EC_{50}$ (μM) Mean ± SEM | IFN-α Maximum (pg/mL) Mean ± SEM |
|---|---|---|
| D60-1 | 0.0353 ± 0.0014 | 2819 ± 1295 |
| D60-2 | 0.0220 ± 0.0066 | 1919 ± 839 |
| D60-3 | 0.0228 ± 0.0433 | 2473 ± 1068 |
| D60-4 | 0.0285 ± 0.0050 | 2893 ± 1300 |
| D60-5 | 0.0293 ± 0.0083 | 2965 ± 1340 |
| D60-6 | 0.0238 ± 0.0055 | 2902 ± 1335 |
| D60-7 | 0.0248 ± 0.0088 | 1869 ± 856 |
| D60-8 | 0.0253 ± 0.0077 | 1647 ± 813 |

Example 2

Assessment of Polynucleotides in Mice

Activity of polynucleotides (PN) was assessed in vivo by measurement of cytokines in bronchoalveolar lavage fluid (BALF), histopathological scoring of lung tissue, and determination of changes in body weight of mice following intranasal administration of saline, D60-1, or D60-7 on a biweekly schedule.

Saline or a polynucleotide TLR9 agonist at a dose of 1, 5, or 20 μg was administered to BALB/c mice (n=5/group) via the intranasal route in a volume of 50 μL to ensure delivery to the lungs. Mice were given intranasal treatments on Days 0, 14, 28, and 42, for a total of four treatments. The mice were weighed twice weekly. Twenty-four hours after the last (fourth) treatment, mice were sacrificed and bronchoalveolar lavage was performed with saline to obtain a liquid wash of the lower respiratory tract. Subsequently, lung tissue was harvested and preserved in 10% formalin for paraffin embedding, sectioning and staining with hematoxylin and eosin in preparation for histopathological assessment and scoring. Lung tissue sections were scored on a scale of 1 to 5 with 1 representing non-changed lungs and higher scores representing increased incidence of peri-bronchiolar and peri-vascular inflammatory infiltrates, as well as increased incidence of structural changes and lung tissue remodeling. Cytokine levels in BALF were measured using the MAG-PIX® multiplex system (Luminex, Austin, Tex.).

Figure 3A:
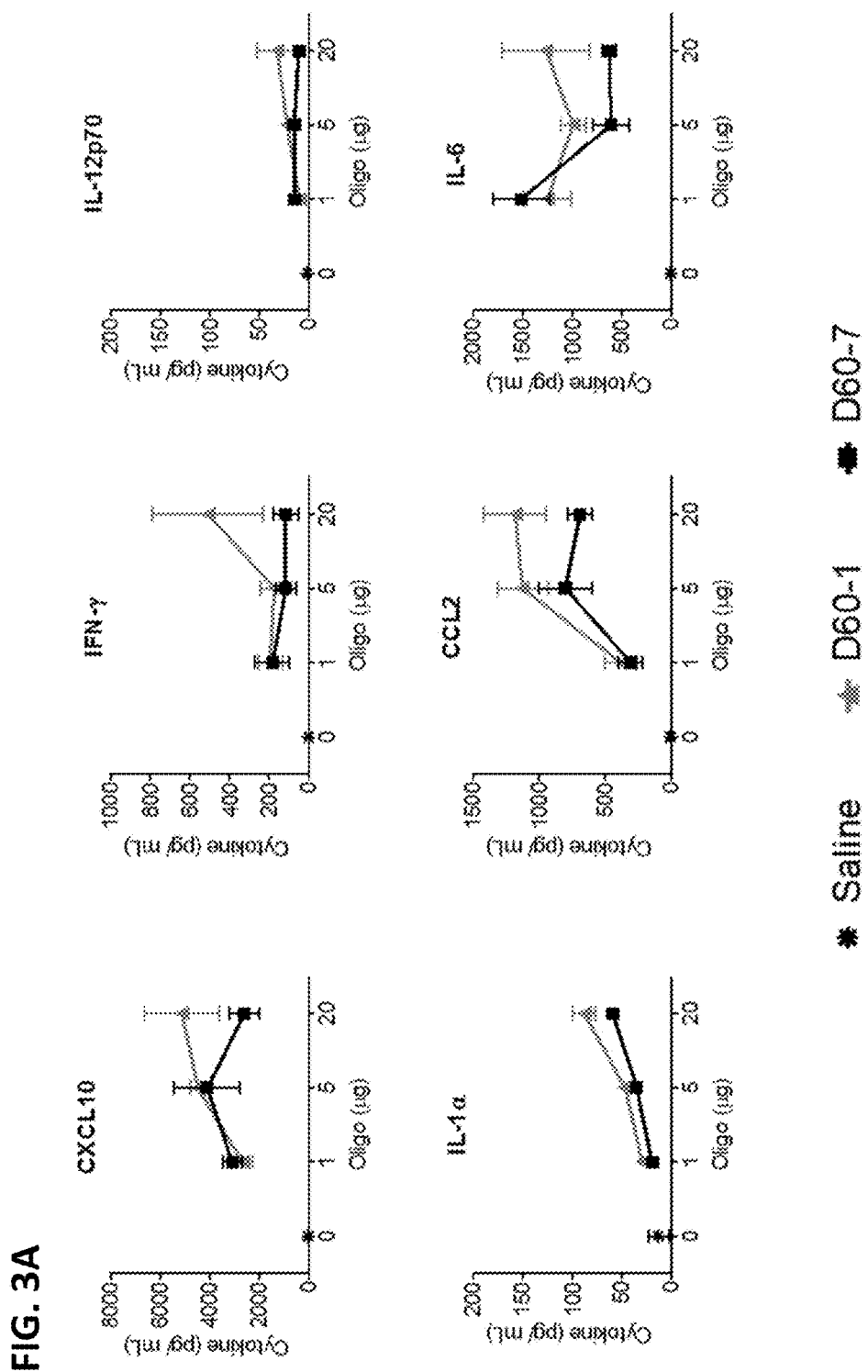
FIG. 3A-B shows multiple graphs depicting levels of cytokines in the bronchoalveolar lavage fluid (BALF) of mice following intranasal administration of saline, polynucleotide TLR9 agonist D60-1, or polynucleotide TLR9 agonist D60-7, at 1, 5, or 20 µg on Days 0, 14, 28, and 42. The BALF was obtained 24 hours after the fourth treatment. Data shown as Mean±SEM.
Figure 3B:
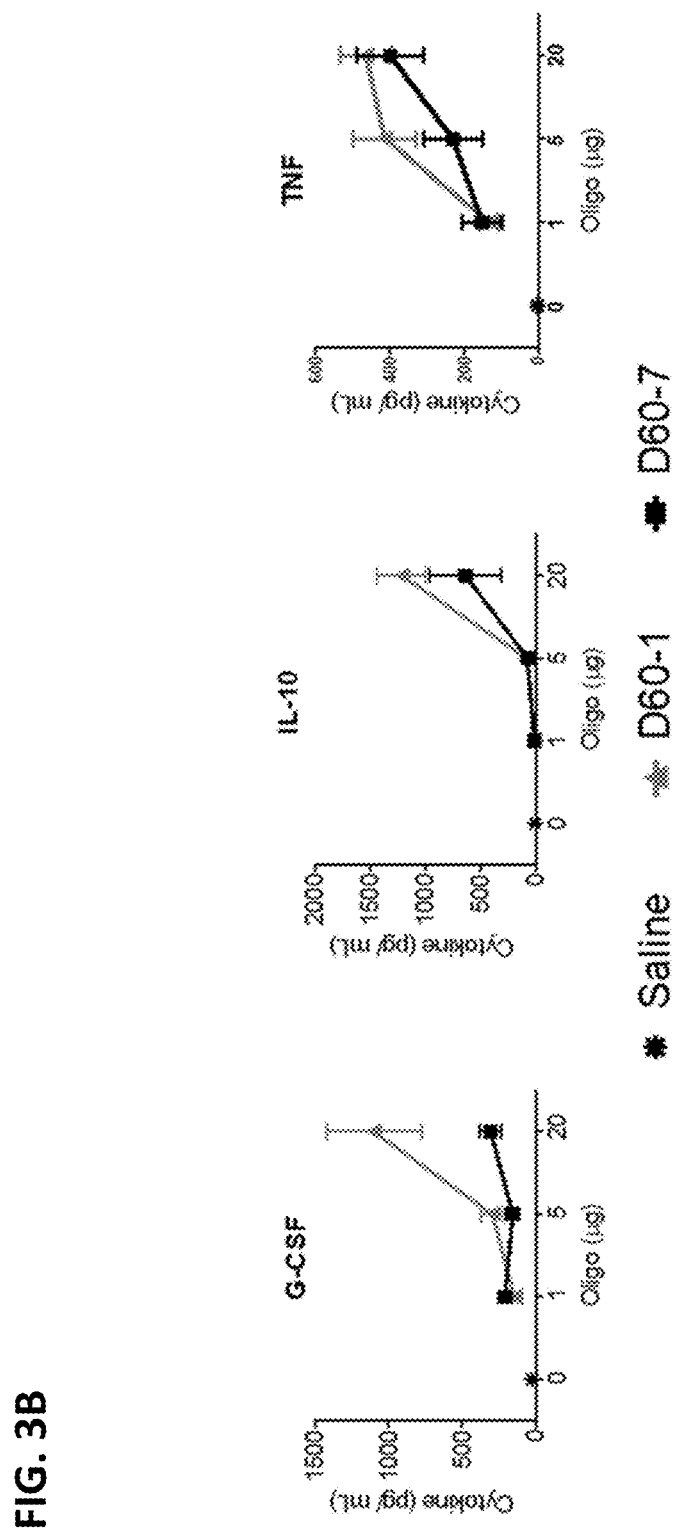

Administration of polynucleotide TLR9 agonists via the intranasal route induces a local immune response as determined by measuring cytokines in BALF (FIG. 3). At the lower doses tested (1 or 5 µg), D60-1 and D60-7 induced comparable levels of many cytokines. However, at the highest dose tested (20 µg or about 1 mg/kg dose), D60-1 induced higher levels of all cytokines as compared to D60-7.

Figure 4:
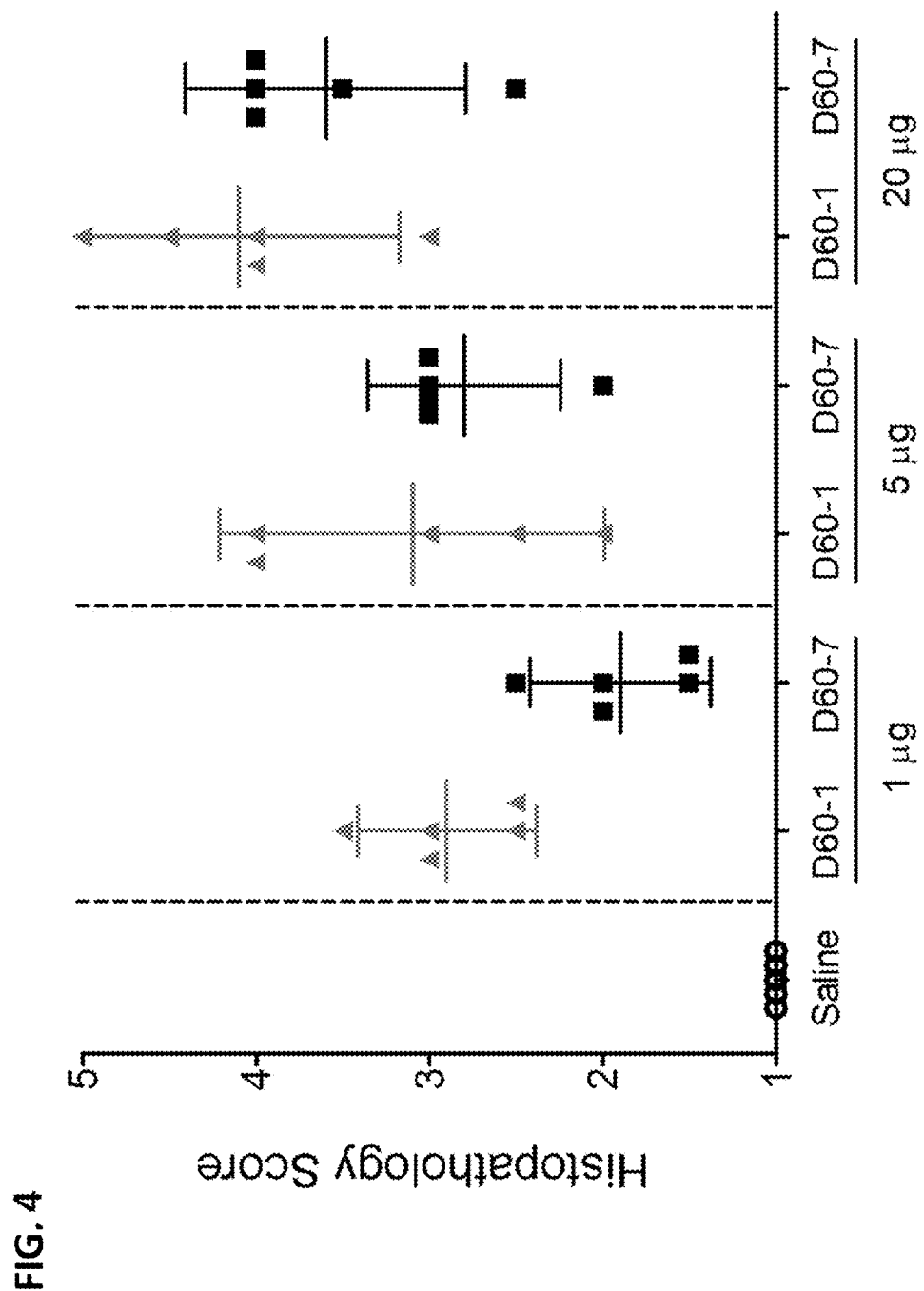
FIG. 4 is a graph illustrating histopathological scores of lung tissue from mice following intranasal administration of saline, polynucleotide TLR9 agonist D60-1 or polynucleotide TLR9 agonist D60-7, at 1, 5, or 20 µg on Days 0, 14, 28, and 42. Mice were sacrificed and lung samples were harvested 24 hours after the fourth treatment. Data shown as Mean with 95% Confidence Intervals.
Figure 5:
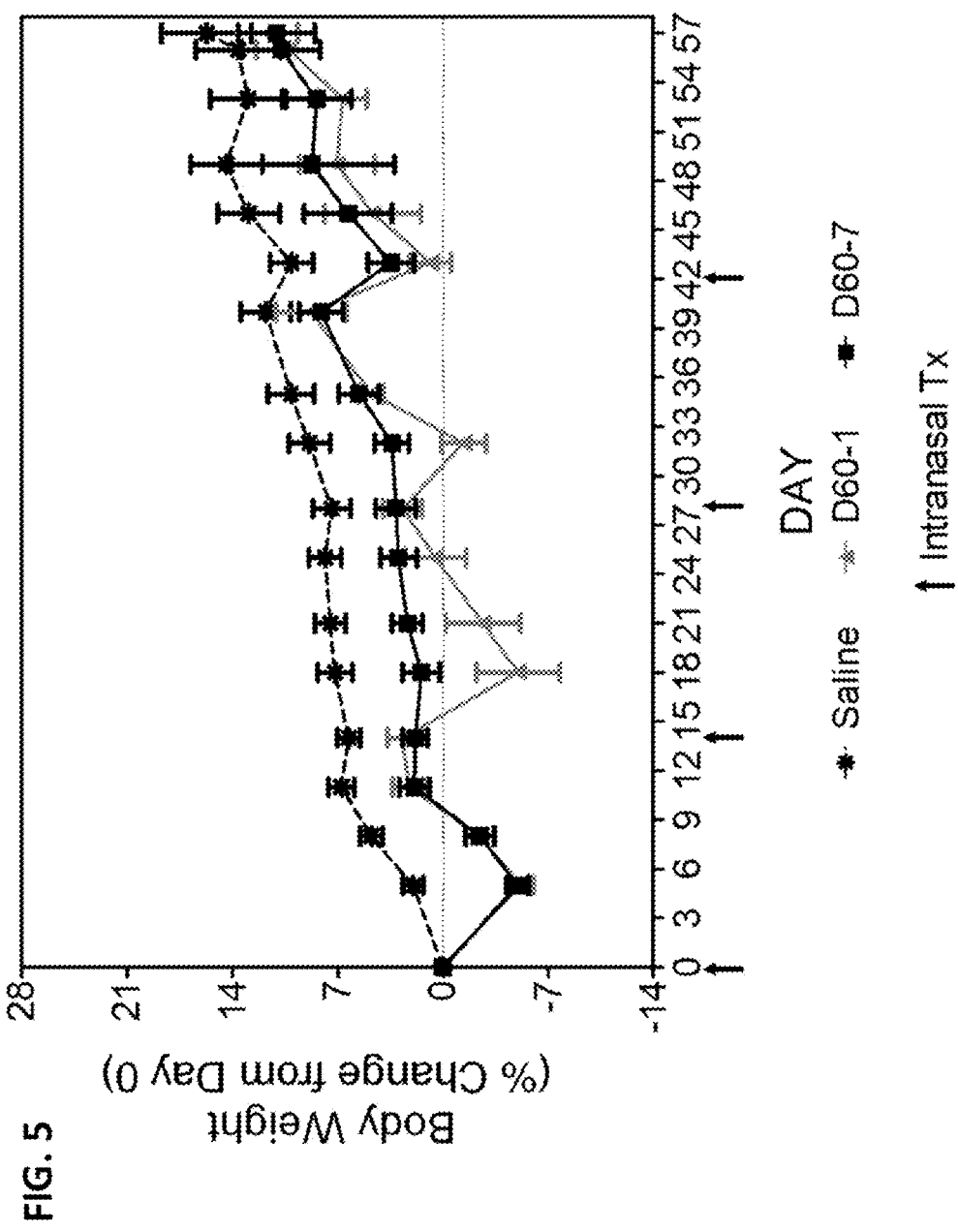
FIG. 5 is a graph showing changes in body weight (percentage of baseline) of mice following intranasal administration of saline, 20 µg polynucleotide TLR9 agonist D60-1, or 20 µg polynucleotide TLR9 agonist D60-7, on Days 0, 14, 28, and 42. Data shown as Mean±SEM.

Polynucleotide induced toxicity was observed locally by microscopic examination of lung tissue and systemically by measuring changes in body weight (Campbell et al., J Clin Invest, 119:2564-2576, 2009). Histopathological scoring of lung tissue sections captured dose-depended increases in peri-bronchiolar and peri-vascular cellular infiltration, changes to airway and blood vessel walls and tissue remodeling in response to both D60-1 and D60-7 with more pronounced effects, at each dose level, in recipients of D60-1 (FIG. 4). At the highest dose tested (20 µg) D60-1 caused more pronounced post-treatment weight loss than D60-7, especially after the $2^{nd}$ and $3^{rd}$ treatments on Days 14 and 28, respectively (FIG. 5). Taken together, these data indicate that intranasal administration of D60-7 is associated with reduced toxicity as compared to D60-1.

Example 3

Assessment of Polynucleotides in Mouse Models of Cancer of the Lung

Activity of polynucleotides (PN) is assessed in vivo in several different mouse models of metastatic cancer to the lung (Heppner et al., Breast Cancer Res. 2:331-334, 2000).
Subcutaneous (SC) Injection of Carcinoma Cells.

D60-7 and anti-PD-1 Synergize to Increase Survival of Mice Bearing Lung Tumors

Figure 6:
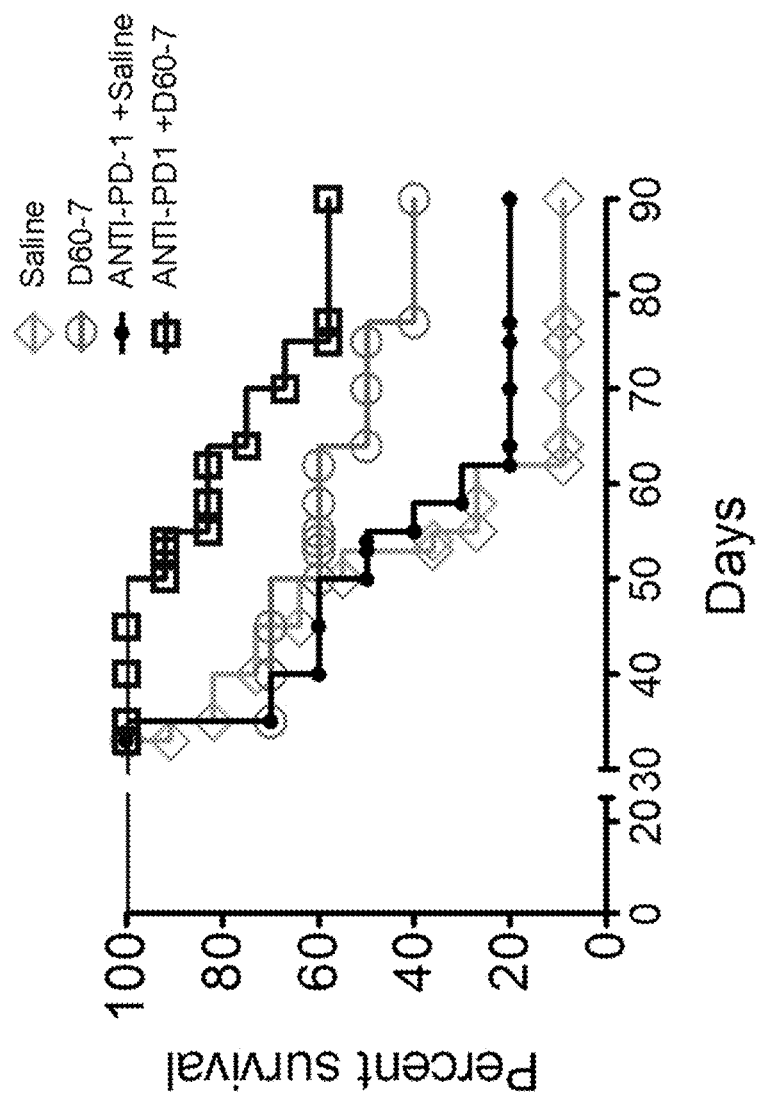
FIG. 6 shows survival of mice bearing metastatic tumor 4T1 treated with intra-pulmonary D60-7, systemic anti-PD-1 antibody or a combination of the two agents.

4T1 breast carcinoma cells spontaneously metastasize from the subcutaneous space to the lung, liver, pancreas, bones and blood. About 10,000 4T1 cells were injected subcutaneously into BALB/c mice. Six days later treatment with an anti-PD-1 blocking antibody (Ab) was initiated. Blocking Ab was administered by IP injection at a dose of 250 µg every 3 or 4 days for 5 weeks. The primary tumor was surgically removed at day 15. The polynucleotide TLR9 agonist D60-7 was administered intranasally at a dose of 10 µg in 50 µL saline starting on day 16 and twice a week thereafter for three weeks (e.g., on days 16, 19, 23, 26, 30, 34, and 41). The polynucleotide TLR9 agonist (D60-7) and the blocking Ab (anti-PD-1) were given alone, or in combination. Saline was administered as a control to a separate group of mice and to the mice receiving anti-PD-1 alone. The number of mice per group was as follows: saline (control) n=11; D60-7 n=10; anti-PD-1 n=10; anti-PD-1 plus D60-7 n=12. The ability of treatments to increase survival of tumor bearing mice was evaluated for 90 days. FIG. 6 is a composite of two independent experiments showing enhanced survival of mice treated with both D60-7 and anti-PD-1, compared to mice treated with either agent alone.

D60-7 and anti-PD-1 Synergize to Reduce Number of Lung Metastasis

Figure 7:
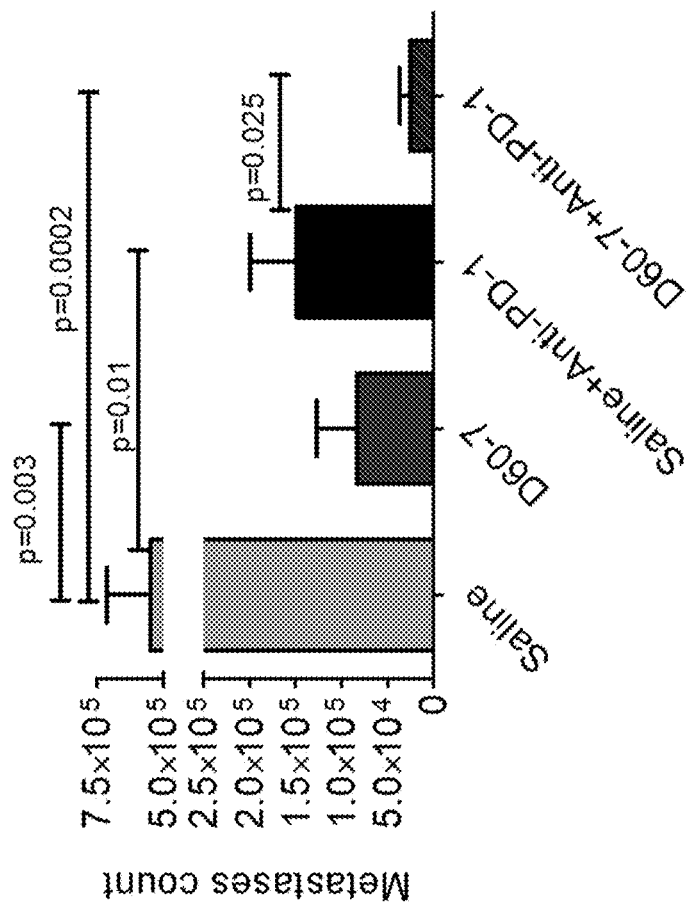
FIG. 7 shows the number of metastatic 4T1 cells in the lungs of mice treated with intra-pulmonary D60-7, systemic anti-PD-1 antibody or a combination of the two agents.

About 10,000 4T1 cells were injected subcutaneously into BALB/c mice. Six days later treatment with an anti-PD-1 blocking antibody was initiated. Anti-PD-1 was administered by IP injection at a dose of 250 µg twice a week from day 6 to day 34. The primary tumor was surgically removed at day 15. D60-7 was administered intranasally at a dose of 10 µg in 50 µL saline on days 16, 19, 21, 23, 27, and 30. D60-7 and anti-PD-1 were given alone, or in combination. Saline was administered as a control to a separate group of mice and to the mice receiving anti-PD-1 alone. On day 34, mice were sacrificed. Lungs were harvested and processed to count the number of lung metastasis by plating assay. In brief, lungs were cut 15 times with scissors and digested for 30 min at 37° C. in 5 ml of HBSS containing 1 mg/mL collagenase type IV and 0.25 mg/mL DNase I. After incubation the suspension was washed twice with HBSS and resuspended in 5 ml of tissue culture medium (RPMI plus 10% FBS). The suspension was diluted in 10 ml of tissue culture medium at different dilutions ranging from 1:2 to 1:1000 and plated in petri dishes. After 10 days, tumors colonies were counted to assess the number of metastatic colony forming cells in the lung. The number of mice per group was as follows: saline (control) n=13; D-60-7 n=11; anti-PD-1 n=14; anti-PD-1 plus D60-7 n=14. FIG. 7 is cummulative of two independent experiments showing that both D60-7 or anti-PD-1 led to significant reductions in the number of metastases as single agents. Strikingly, the combination of D60-7 or anti-PD-1 synergized to produce an even greater reduction in the number of lung metastases. P values were calculated using Prism software using unpaired Mann Whitney unpaired T test.
Intravenous (IV) Injection of Carcinoma Cells.

About 20,000 CT26 colon carcinoma cells are injected intravenously into BALB/c mice, or about 50,000 Lewis lung carcinoma cells are injected intravenously into C57BL/6 mice. Either an anti-PD-1 or an anti-PDL-1 blocking antibody (Ab) is administered by IP injection at a dose of 250 µg on days 7, 11, 15, 18, 21, 25, 28 and 32. A polynucleotide TLR9 agonist is administered intranasally at a dose of 10 or 5 or 1 µg in 50 µL saline on days 7, 11, 15, 18, 21, 25, 28, and 32. The polynucleotide TLR9 agonist and the blocking Ab are given alone, or in combination. The ability of treatments to increase survival of tumor bearing mice is evaluated for up to 200 days.

We claim:

1. A method of treating cancer of the lung in a mammalian subject in need thereof, the method comprising administering to the subject an effective amount of a polynucleotide by intrapulmonary delivery, wherein the polynucleotide consists of the sequence of: 5'-TCGTAACGTTCGAACGTTC-GANx-3' (SEQ ID NO:2), wherein x is 0, 1 or 2, each N is A, C or T, and wherein at least one internucleotide linkage is a phosphorothioate linkage.

2. The method of claim 1, wherein the polynucleotide consists of SEQ ID NO:7, SEQ ID NO:8, or SEQ ID NO:9.

3. The method of claim 1, wherein the polynucleotide is double stranded.

4. The method of claim 1, wherein all of the internucleotide linkages are phosphorothioate linkages.

5. The method of claim 1, wherein the subject has a primary cancer selected from the group consisting of primary lung cancer and extrapulmonary cancer.

6. The method of claim 1, wherein the cancer of the lung is primary lung cancer.

7. The method of claim 6, wherein the primary lung cancer is non-small-cell lung carcinoma (NSCLC) or small-cell lung carcinoma (SCLC).

8. The method of claim 1, wherein the cancer of the lung is metastatic cancer to the lung.

9. The method of claim 8, wherein the metastatic cancer is a metastasis of a primary cancer selected from the group consisting of bladder cancer, breast cancer, colorectal cancer, head and neck cancer, kidney cancer, melanoma, pancreatic cancer, prostate cancer, and ovarian cancer.

10. The method of claim 1, wherein the mammalian subject is a human.

11. The method of claim 1, further comprising administering an effective amount of a second therapeutic agent to the subject.

12. The method of claim 11, wherein the second therapeutic agent comprises a chemotherapeutic agent selected from the group consisting of actinomycin, afatinib, alectinib, asparaginase, azacitidine, azathioprine, bicalutamide, bleomycin, bortezomib, camptothecin, carboplatin, capecitabine, certinib, cisplatin, chlorambucil, crizotinib, cyclophosphamide, cytarabine, daunorubicin, docetaxel, doxifluridine, doxorubicin, erlotinib, epirubicin, epothilone, etoposide, fludarabine, flutamine, fluorouracil, gefitinib, gemcitabine, hydroxyurea, idarubicin, ifosfamide, imatinib, irinotecan, lapatinib, letrozole, mechlorethamine, mercaptopurine, methotrexate, mitomycin, mitoxantrone, octreotide, oxaliplatin, paclitaxel, pemetrexed, raltitrexed, sorafenib, sunitinib, tamoxifen, temozolomide, teniposide, tioguanine, topotecan, valrubicin, vinblastine, vincristine, vindesine, vinorelbine, and combinations thereof.

13. The method of claim 12, wherein the chemotherapeutic agent comprises one or more of the group consisting of cyclophosphamide, doxorubicin, and vincristine.

14. The method of claim 12, wherein the chemotherapeutic agent comprises one or more of the group consisting of mitomycin, vindesine and cisplatin.

15. The method of claim 12, wherein the chemotherapeutic agent comprises one or both of the group consisting of cisplatin and vinorelbine.

16. The method of claim 12, wherein the chemotherapeutic agent comprises one or both of the group consisting of cisplatin, etoposide and ifosfamide.

17. The method of claim 11, wherein the second therapeutic agent is an antagonist of an inhibitory immune checkpoint molecule.

18. The method of claim 17, wherein the inhibitory immune checkpoint molecule is selected from the group consisting of PD-1, PD-L1, PD-L2, CTLA-4(CD152), LAG-3, TIM-3, TIGIT, IL-10, and TGF-beta.

19. The method of claim 17, wherein the inhibitory immune checkpoint molecule is indoleamine 2,3-dioxygenase (IDO) or tryptophan 2,3-dioxygenase (TDO).

20. The method of claim 11, wherein the second therapeutic agent is an agonist of an immune stimulatory molecule.

21. The method of claim 20, wherein the immune stimulatory molecule is selected from the group consisting of CD27, CD40, OX40 (CD134), GITR, CD137, CD28 and ICOS (CD278).

22. The method of claim 11, wherein the second therapeutic agent comprises an antibody, fragment or derivative thereof.

23. The method of claim 5, further comprising one or both of resecting the primary cancer and administering radiation therapy.

24. The method of claim 11, wherein the effective amount of the polynucleotide and the effective amount of the second therapeutic agent together result in a synergistic effect against the cancer of the lung.

25. The method of claim 11, wherein the effective amount of the polynucleotide and the effective amount of the second therapeutic agent together result in an additive effect against the cancer of the lung.

26. The method of claim 11, wherein the effective amount of the polynucleotide and the effective amount of the second therapeutic agent together result in a cooperative effect against the cancer of the lung.

27. The method of claim 5, wherein treating cancer of the lung comprises one or more of the following:
  (a) increasing survival time of the subject;
  (b) reducing volume of the primary cancer;
  (c) retarding growth of the primary cancer;
  (d) reducing number of metastatic tumors;
  (e) reducing volume of metastatic tumors; and
  (f) retarding growth of metastatic tumors.

28. The method of claim 1, wherein treating cancer of the lung comprises inducing secretion in the lung of one or more cytokines selected from the group consisting of chemokine CC motif ligand 2 (CCL2), chemokine CXC motif ligand 10 (CXCL10), interferon-alpha (IFN-α), interferon-gamma (IFN-γ), interleukin-1alpha (IL-1α), interleukin-6 (IL-6), interleukin-10 (IL-10), interleukin-12 p70 (IL-12 p70), granulocyte colony-stimulating factor (GCSF), and tumor necrosis factor-alpha (TNF-α).

29. The method of claim 1, wherein treating cancer of the lung does not result in polynucleotide-induced toxicity of the lung of such severity that repeated administration of the polynucleotide is contraindicated.

30. The method of claim 1, wherein treating cancer of the lung does not result in polynucleotide-induced flu-like symptoms of such severity that repeated administration of the polynucleotide is contraindicated, wherein the flu-like symptoms comprise one or more of the group consisting of fever, headache, chills, myalgia and fatigue.

31. A method of treating cancer in a mammalian subject in need thereof, comprising: administering a pharmaceutical composition to the subject in an amount sufficient to treat cancer in the subject, wherein the pharmaceutical composition comprises an isolated polynucleotide and pharmaceutically acceptable excipient, and the polynucleotide consists of the sequence of: 5'-TCGTAACGTTCGAACGTTC-GANx-3' (SEQ ID NO:2), wherein x is 0, 1 or 2, each N is A, C or T, and wherein at least one internucleotide linkage is a phosphorothioate linkage.

32. The method of claim 31, wherein the pharmaceutical composition is administered to the subject by intrapulmonary administration.

33. The method of claim 32, wherein the intrapulmonary administration involves use of a device selected from the group consisting of a nebulizer, a metered-dose inhaler, a sprayer, and a dry-powder inhalation device.

34. The method of claim 31, wherein the pharmaceutical composition is administered by injection through a route selected from the group consisting of intravenous, intramuscular, and subcutaneous.

35. The method of claim 31, wherein the polynucleotide consists of SEQ ID NO:7, SEQ ID NO:8, or SEQ ID NO:9.

* * * * *

SEQUENCE LISTING

```
<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: Synthetic Construct

<400> SEQUENCE: 1
tcgaacgttc gaacgttcga acgttcgaat                                      30

<210> SEQ ID NO 2
```

```
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 22, 23
<223> OTHER INFORMATION: n = A, C or T and up to 2 of them can be
      present or absent

<400> SEQUENCE: 2
tcgtaacgtt cgaacgttcg ann                                           23

<210> SEQ ID NO 3
<211> LENGTH: 27
<212> TYPE: DNA
<213> ORGANISM: Artificial Sequence
<220> FEATURE:
<223> OTHER INFORMATION: Synthetic Construct

<400> SEQUENCE: 3
tcgtaacgtt cgaacgttcg aacgtta                                       27

<210> SEQ ID NO 4
<211> LENGTH: 26
<212> TYPE: DNA
<213> ORGANISM: Artificial Sequence
<220> FEATURE:
<223> OTHER INFORMATION: Synthetic Construct

<400> SEQUENCE: 4
tcgtaacgtt cgaacgttcg aacgtt                                        26

<210> SEQ ID NO 5
<211> LENGTH: 25
<212> TYPE: DNA
<213> ORGANISM: Artificial Sequence
<220> FEATURE:
<223> OTHER INFORMATION: Synthetic Construct

<400> SEQUENCE: 5
tcgtaacgtt cgaacgttcg aacgt                                         25

<210> SEQ ID NO 6
<211> LENGTH: 24
<212> TYPE: DNA
<213> ORGANISM: Artificial Sequence
<220> FEATURE:
<223> OTHER INFORMATION: Synthetic Construct

<400> SEQUENCE: 6
tcgtaacgtt cgaacgttcg aacg                                          24

<210> SEQ ID NO 7
<211> LENGTH: 23
<212> TYPE: DNA
<213> ORGANISM: Artificial Sequence
<220> FEATURE:
<223> OTHER INFORMATION: Synthetic Construct

<400> SEQUENCE: 7
tcgtaacgtt cgaacgttcg aac                                           23

<210> SEQ ID NO 8
<211> LENGTH: 22
<212> TYPE: DNA
```

```
<213> ORGANISM: Artificial Sequence
<220> FEATURE:
<223> OTHER INFORMATION: Synthetic Construct

<400> SEQUENCE: 8
tcgtaacgtt cgaacgttcg aa                                          22

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
tcgtaacgtt cgaacgttcg a                                           21
```